(12) United States Patent
Ma et al.

(10) Patent No.: US 8,088,599 B2
(45) Date of Patent: Jan. 3, 2012

(54) NUCLEIC ACIDS ENCODING GENETICALLY MODIFIED TISSUE FACTOR PATHWAY INHIBITOR (TFPI) AND METHOD OF MAKING THE SAME

(75) Inventors: Duan Ma, Shanghai (CN); Jingui Mu, Shanghai (CN); Jiping Wang, Shanghai (CN); Huijun Wang, Shanghai (CN); Wang Liang, Shanghai (CN)

(73) Assignee: Fudan University, Shanghai (CN)

( * ) Notice: Subject to any disclaimer, the term of this patent is extended or adjusted under 35 U.S.C. 154(b) by 253 days.

(21) Appl. No.: 12/407,529

(22) Filed: Mar. 19, 2009

(65) Prior Publication Data
US 2010/0204095 A1 Aug. 12, 2010

(30) Foreign Application Priority Data
Feb. 6, 2009 (CN) .......................... 2009 1 0016024

(51) Int. Cl.
C12P 21/06 (2006.01)
C12N 1/00 (2006.01)
C12N 15/00 (2006.01)
C12N 15/74 (2006.01)

(52) U.S. Cl. ............... 435/69.1; 435/254.23; 435/320.1; 435/471

(58) Field of Classification Search .................. None
See application file for complete search history.

(56) References Cited

U.S. PATENT DOCUMENTS

| 5,212,091 | A | 5/1993 | Diaz-Collier et al. |
| 5,346,991 | A | 9/1994 | Roy et al. |
| 5,589,359 | A | 12/1996 | Innis et al. |
| 5,739,101 | A | 4/1998 | Roy et al. |
| 5,773,251 | A | 6/1998 | Wun et al. |
| 5,888,968 | A | 3/1999 | Chen et al. |
| 6,103,500 | A | 8/2000 | Innis et al. |
| 6,989,369 | B2 * | 1/2006 | Ladner et al. .................. 514/1.5 |
| 2005/0037475 | A1 | 2/2005 | Reifsnyder |
| 2009/0018069 | A1 | 1/2009 | Bajaj |
| 2009/0170766 | A1 * | 7/2009 | Oehme et al. ................... 514/12 |

FOREIGN PATENT DOCUMENTS

CN 03151203.8 9/2004
WO PCT/US2004/000234 3/2005

OTHER PUBLICATIONS

De Schutter K, et al. Nature Biotechnology 27(6):561-569, Jun. 2009.*
Invitrogen catalog, p. 19-23, 1998.*
Pogulis RJ, et al. Methods in Molecular Biology (Humana Press, Clifton N.J.), 57:167-176, 1996.*
Effect of Cholesterol Lowering on Intravascular Pools of TFPI and . . . , Arteriosclerosis, Thrombosis, and Vascular Biology: 1995;15:879-885.
Characterization of Human Tissue Factor Pathway Inhibitor . . . , The Journal of Biological Chemistry: vol. 268, No. 18, Issue: Jun. 25, pp. 13344-13351,1993.
The Carboxy Terminus of Tissue Factor Pathway Inhibitor Is Required . . . , J. Clin. Invest. vol. 95, Apr. 1995, 1773-1781.
Inhibitory Properties of Full-length and Truncated Recombinant TFPI, The Journal of Biological Chemistry: vol. 268, No. 12, Issue of Apr. 25, pp. 8704-8710,1993.

* cited by examiner

*Primary Examiner* — Robert Landsman
(74) *Attorney, Agent, or Firm* — Yuan Qing Jiang

(57) ABSTRACT

The present invention provides long half life genetically modified TFPI sequences (LTFPI) for anticoagulation. On the genetically modified TFPI sequence, the lysine at the carboxy-terminal sites 241, 254, 260 and 261 are replaced by alanin and the amino acid asparagine at glycosylation sites 117, 167, 228 and the amino acids serine and threonine at glycosylation sites 174 and 175 are substitutionally mutated. The present invention also provides methods of making the LTFPI through high efficient LTFPI expression from yeast production system.

6 Claims, 4 Drawing Sheets

NUCLEIC ACIDS ENCODING GENETICALLY MODIFIED TISSUE FACTOR PATHWAY INHIBITOR (TFPI) AND METHOD OF MAKING THE SAME

FIELD OF INVENTION

The present invention relates to genetically modified TFPI sequences, and more particularly, genetic modified long half life TFPI sequences capable of protein expression in at least yeast cell.

BACKGROUND OF INVENTION

Tissue factor pathway inhibitor (TFPI) is a serine protease inhibitor synthesized primarily by vascular endothelial cell. It functions as an anticoagulant, regulating tissue factor (TF) induced cascade of blood coagulation.

Under physiology condition, TF triggers extrinsic pathway of blood coagulation during hemostasis. TF binds factor VIa, which is a serine protease, and forms a complex with it. The complex in turn catalyzes the conversion of another inactive protease factor X into the active protease factor Xa and subsequently activating the entire extrinsic pathway of blood coagulation.

However, TF may function undesirably under pathologic condition. It is believed that the extrinsic pathway of blood coagulation triggered by TF plays a major role in thrombogenesis associated with atherosclerosis, particularly under the condition when an atheromatous plaque ruptures. TF triggered blood coagulation also plays negative roles under other pathological conditions such as myocardial infarction, ischemia, cerebrovascular disease, pulmonary thromboembolism, deep vein thrombosis, DIC and sepsis.

TFPI is a natural inhibitor to TF and blocks the extrinsic pathway of blood coagulation. TFPI inhibits factor Xa (FXa) directly, and inactivates the activity of the complex formed by factor VIIa-TF (FVIIa-TF), either with TF in suspension or with TF expressed on the surface membranes of perturbed endothelial cells, thereby stopping the cascade process of extrinsic pathway.

Structurally, wild type TFPI is a protein with molecular weight of 42-48 KD. The protein has three N-glycosylation sites on 117, 167, 228 on it. During its expression in yeast, the protein may have one more potential glycosylation site on 174 or 175.

The TFPI molecular weight varies due to the difference of sugar moiety side chains on the glycosylation sites of the protein. Glycosylation sites and sugar moieties attaching on the sites vary in different species.

The precursor TFPI molecule includes a 28 amino acid residues signal peptide. After cleavage, it gives a mature protein with 276 amino acid residues, including the N terminal which is rich in acidic amino acid residues and is highly negative in charge, followed by 3 tandem Kunitz protease inhibitory domains and a carboxyl terminal (C terminal) which is rich in basic amino acid residues and is highly positive in charge. The 3 tandem Kunitz domains are called K1, K2 and K3 respectively. K2 domain binds Factor Xa (FXa) directly and suppresses its activity. K1 domain binds Factor VIIa/TF (F VIIa/TF) via TF-Factor VIa complex, resulting in the formation of the quaternary complex TF/FVIIa/TFPI/FXa, which is devoid of enzymatic activity, and inhibiting blood coagulation. The function of K3 domain remains unknown.

It has been an avid research field to utilize TFPI's function as a natural anticoagulant to block blood coagulation and treat thrombogenesis such as atherosclerosis in patients.

For example, U.S. Pat. No. 5,888,968 discloses a pharmaceutical composition containing TFPI for patients suffering from in *E. coli* sepsis. TFPI may also be used to treat blood coagulation and lower cholesterol (Effect of Cholesterol Lowering on Intravascular Pools of TFPI and Its Anticoagulant Potential in Type II Hyperlipoproteinemia, Arteriosclerosis, Thrombosis, and Vascular Biology. 1995;15:879-885.)

One of the major obstacles of clinical application of wild type TFPI as an anticoagulation drug is that natural TFPI's half life is short, seriously limiting its application clinically.

The other problem is that the yield of TFPI in lab production is low and unstable. TFPI is currently produced in prokaryotic expression system and eukaryotic expression system. *E coli* expression system expresses TFPI in inclusion bodies (U.S. Pat. No. 5,212,091, US patent application publication 20050037475). Complex processes such as renaturing the protein which is a process folding the protein according to its natural 3-dimensional structure from human source, have to be employed in order to obtain active TFPI protein after the product is expressed in a prokaryotic system. The final product yield of active TFPI in a prokaryotic system is low because of the after expression processes.

Eukaryotic expression systems such as CHO (Chinese hamster Ovary cell), BHK (Baby Hamster Kidney cell), mouse C127 and yeast *Saccharomyces cereuisiae* (Characterization of Human Tissue Factor Pathway Inhibitor Variants Expressed in *Saccharomyces cereuisiae*, The Journal Of Biological Chemistry, Vol. 268, No. 18, Issue of June 25, pp. 13344-13351,1993) have the advantage of producing folded TFPI protein, and are currently used in lab production of TFPI. However, the protein obtained from this method is just a protein having 1-161 amino acid residues, not a full length TFPI. Furthermore, some of the eukaryotic expression systems are troublesome, with low quantity of active TFPI expression and high cost. On the other hand, no document shows that TFPI can be expressed in *Pichia.pastoris*. Some research indicates that *Pichia.pastoris* system can not be used to express TFPI.

Therefore, several issues have to be addressed before active TFPI can be used in clinical practice. Long half life TFPI (LTFPI) with no immunogenesis has to be developed, and current eukaryotic expression systems need to be improved to produce high quality and stable TFPI.

SUMMARY OF THE INVENTION

One objective in accordance with the present invention is to provide a method to produce the optimized DNA sequence of TFPI which can be expressed and translated into LTFPI in yeast cell.

Another objective is to provide a genetically modified TFPI which has long half life and therefore is capable of inhibiting TF and blocking blood coagulation.

In one aspect of the invention, the invention advantageously provides a genetically modified TFPI DNA sequence which is optimized according to the sequence of three adjacent nucleotides constituting the genetic codons preferred by yeast; meanwhile the codon of the lysine at the carboxy-terminal sites 241, 254, 260 and 261 are replaced by the codons of alanin and the codons of the amino acid asparagine at glycosylation sites 117, 167, 228 and the codons of the amino acid asparagine at glycosylation sites 174 and 175 are also substitutionally mutated.

In another aspect of the invention, provided is a pharmaceutical composition for anticoagulation comprising a pharmaceutically effective amount of a genetically modified TFPI sequence wherein the lysine at the carboxy-terminal sites 241, 254, 260 and 261 are replaced by alanin and the amino acid asparagine at glycosylation sites 117, 167, 228 and the amino acid asparagine at glycosylation sites 174 and 175 are substitutionally mutated.

Yet, in another aspect of the invention, provided is a method of producing genetically modified TFPI comprising: (a) providing an optimized mutant TFPI DNA sequence which is capable of expression in a yeast cell; (b) recombining the optimized mutant TFPI sequence with a plasmid of the yeast cell; (c) transforming the plasmid into the yeast cell; (d) culturing the transformed yeast cell; (e) collecting the optimized mutant TFPI from supernatant of the cultured yeast cell; and (f) separating and purifying the collected mutant TFPI.

Additional features and advantages of the invention will be apparent from the detailed description which follows, taken in conjunction with the accompanying figures, which together illustrate, by way of example, features of the invention.

DETAILED DESCRIPTION OF THE INVENTION

Figure 1A:
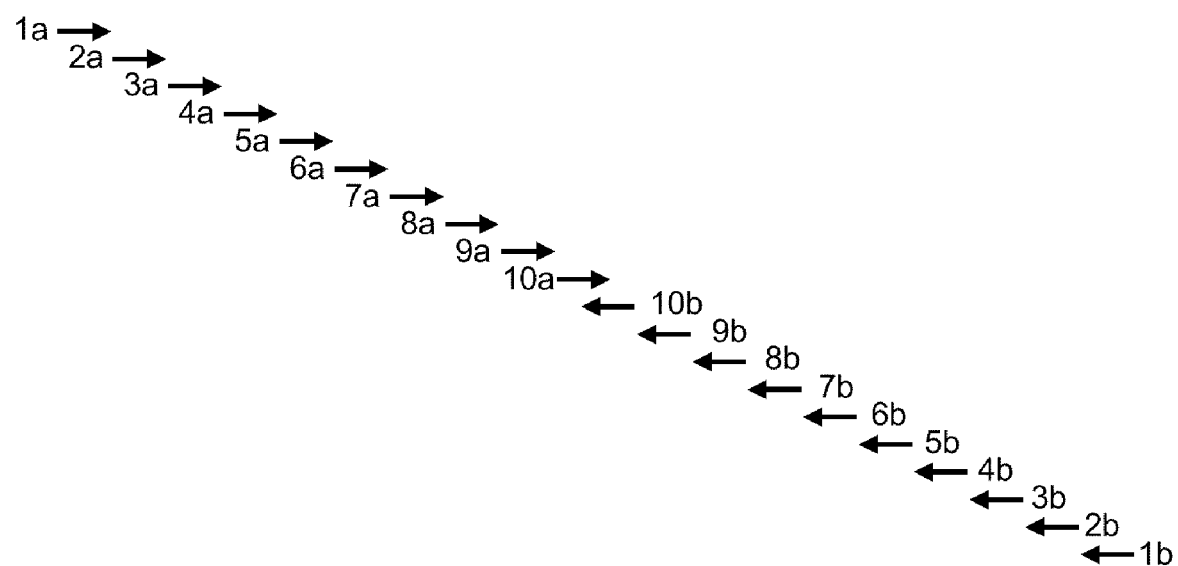
FIG. 1a shows diagram of 10 steps of synthesizing long half life TFPI (LTFPI) by overlap-extension PCR (O-E PCR) from 10 pairs of primers (primer 10a, 10b through 1a, 1b).

In accordance with one embodiment of the present invention, long half life TFPI (LTFPI) is developed by genetically modifying wild type TFPI, such as mutating and substituting genetic codons of the original DNA sequence of wild type TFPI to overcome the obstacle of short half life of wild type TFPI.

TFPI is catabolized primarily in the liver. The C terminal of TFPI binds low density lipoprotein receptor-related protein (LRP) on liver cell membrane, then TFPI/LRP complex is internalized into the liver cell and degraded. TFPI degradation and elimination is highly correspondent to its C terminal sequence structure, and its binding to LRP is the key to start the process (The Carboxy Terminus of Tissue Factor Pathway Inhibitor Is Required for Interacting with Hepatoma Cells In Vitro and In Vivo, J. Clin. Invest. Volume 95, April 1995, 1773-1781).

The wild type TFPI C terminal sequence sites 241, 254, 260 and 261 have basic amino acid residue lysine. Lysine is positively charged and plays a crucial role in binding to LRP on liver cell membrane. The binding to LRP starts the process of TFPI internalization into the liver cell for degradation.

One embodiment of this invention is to provide a genetically modified LTFPI by replacing the positively charged lysine residues on TFPI C terminal sequence sites 241, 254, 260 and 261 with neutral amino acid residue alanin, by way of substitute mutation of wild type TFPI DNA sequence. Since amino acid residues alanin is neutral and is able to prevent TFPI C terminal from binding to LRP, the process of TFPI internalization into the liver cell for degradation is blocked and the half life of TFPI is prolonged. Therefore LTFPI is produced.

In additional to address the problem of short half life of wild type TFPI, currently research works are in the direction of: 1) Searching and producing modified LTFPI with better anticoagulation property. Particular attentions are focused on K1 and K2 domains since they are known to bind to FVIIa and FXa, and are critical to anticoagulation; 2) Producing naturally folded and low immunogenic TFPI for pharmaceutical application; and 3) Developing a high efficiency, low cost eukaryotic expression system to produce the LTFPI. More mutations on wild type TFPI sequence are attempted. Substitute mutation on Kunitz domain I of TFPI-2 is disclosed to produce plasmin inhibitor for clinical application (US patent application publication 20090018069). U.S. Pat. No. 5,589,359 discloses a chimeric protein providing equivalent or better anticoagulation property, while reducing glycosylated moieties on the Kunitz domains. The process of glycosylation on LTFPI protein (adding side chain sugar moieties onto the protein) and the extent of glycosylation (the number and characteristics of the sugar moieties of the added side chain) of LTFPI in yeast are different from the process and extent in human endothelial cells. It is discovered in this invention that mutating the glycosylation sites on LTFPI DNA sequence and completely eliminating sugar moiety side chains on the protein produce a new mutant LTFPI with anticoagulation effect approximately 3 times potent than that of wild type TFPI (Example 4 of the specification of the invention, mutant LTFPI activity is determined by comparison with the activity of standard from ACTICHROME TFPI Activity Assay Kit produced by American Diagnostica Inc.). Sugar moiety side chains on TFPI are immunogenic. Glycosylation sites on TFPI protein produced by yeast differ from glycosylation sites on TFPI protein produced by human cell, and the subsequent sugar moiety side chain attachments to the protein via glycoslation in yeast are different from that of TFPI synthesized in human endothelial cell naturally in terms of positions and characteristic. Because of the immunogenesis caused by glycosylation differences, TFPI produced from yeast cell can not be used as part of pharmaceutical composition in clinic application. Besides, the folding and forming of three dimensional structure of LTFPI produced by yeast expression are also different from that of TFPI synthesized in human endothelial cell naturally, since the sugar moiety side chains on the protein influence the folding and the forming of three dimensional structure of the protein. In order to solve both immunogenic and folding problems, according to this invention, LTFPI expressed in cultured yeast is mutated at all of the glycosylation sites. The LTFPI is devoid of any sugar moiety side chain attachment and is folded correctly in terms of three dimensional protein structure. Therefore, the new mutant LTFPI completely eliminated sugar moiety side chains produced by expression of genetically modified TFPI DNA sequence in yeast cell is not immunogenic. Thus, a pharmaceutically effective amount of the non immunogenic LTFPI can be used in a composition to treat pathological conditions such as thrombogenesis caused by plaque ruptures in atherosclerosis, myocardial infarction, ischemia, cerebrovascular disease, pulmonary thromboembolism, deep vein thrombosis, DIC and sepsis. LTFPI produced according to this invention has the advantages of 1) naturally folded 3 dimensional protein structure, 2) non immunogenic when it is used as part of pharmaceutical drug, and 3) enhanced anticoagulation activity; 4) extended long half life.

One embodiment of the invention is to provide an optimized mutant LTFPI DNA sequence for eukaryotic expression system by mutating the three N-glycosylation sites on 117, 167, 228 and the potential glycosylation sites on 174 or 175, thereby increasing the expression rate of LTFPI in high efficiency eukaryotic expression system production. In the meantime, the mutant LTFPI produced by the system keeps or enhances its anticoagulation activity. The genetically modified TFPI DNA sequence is characterized by the condons of lysine at the carboxy-terminal sites 241, 254, 260 and 261 are substituted by condons of alanin and the condons of amino acid asparagine at glycosylation sites 117, 167, 228 and the condons of serine and threonine at glycosylation sites 174 and 175 are substitutionally mutated. Specifically, the condons of amino acid asparagines at glycosylation sites 117, 167, 228 are substituted by condons of glutamines, and the condons of amino acid serine at glycosylation sites 174 is substituted by condons of alanin, and the condons of amino acid threonine at glycosylation sites 175 is substituted by condons of alanin. An example of the mutant LTFPI DNA sequence is a sequence represented by SEQ ID NO: 1.

A series of optimization is further performed based on the sequence of TFPI (Chinese patent application number ZL 03151203.8) by using biological information sciences software (Synthetic gene designer) according to genetic codons favored by *Pichia.pastoris*, and is therefore suitable to be expressed in *Pichia.pastoris*. A numbers of new LTFPI sequences are obtained, and are screened to select the best sequence according to the criteria mentioned above (1) naturally folded three dimensional protein structure, 2) non immunogenic when it is used as part of pharmaceutical drug, and 3) enhanced anticoagulation activity). A sequence represented by SEQ ID NO: 1 which is most suitable for *Pichia.pastoris* expression system is selected.

Yet another embodiment of the invention is to provide an optimized eukaryotic expression system to produce LTFPI. *Pichia.pastoris* is a high efficiency yeast expression system used to produce naturally folded protein. *Pichia.pastoris* has a high growth rate and can grow in either shake flasks or a fermenter, which makes it suitable for both small and large scale productions. With its two alcohol oxidase genes, AOX1 and AOX2 which are induced by the addition of methanol, *Pichia* can use methanol as a carbon and energy source. Desired protein expression is under the control of the AOX1 promoter, which means that protein production is induced by adding methanol, and the desired protein is secreted into the growth medium, which greatly facilitates subsequent protein purification.

The advantage of *Pichia.pastoris* expression system over bacterium *Escherichia coli* expression system is that *E. coli* might produce a misfolded protein, which is usually inactive or insoluble.

The advantage of *Pichia.pastoris* expression system over *Saccharomyces cerevisiae* (baker's yeast) expression system is that *Pichia* can easily be grown in cell suspension in reasonably strong methanol solutions that would kill most other micro-organisms, a system that is cheap to set up and maintain. In addition, *Pichia* can grow to very high cell densities and, under ideal conditions, can multiply to the point where the cell suspension is practically a paste. As the protein yield from expression in a microbe is roughly equal to the product of the protein produced per cell and the number of cells, this makes *Pichia* of great use when trying to produce large quantities of protein without expensive equipment. Compared to other expression systems such as S2-cells from Drosophila melanogaster or Chinese Hamster Ovary cells, *Pichia* usually gives much better yields. Cell lines from multicellular organisms usually require complex rich media, including amino acids, vitamins and growth factors. These media significantly limit the large scale production of LTFPI.

However, the structure of the desired protein is important to whether the protein can be expressed in *Pichia.pastoris* system. Some protein can be expressed highly effectively in the system, while some others can not be expressed at all. Therefore, optimization of the gene (DNA) sequence which encodes the primary structure (the sequence) of the protein is highly desirable.

In one embodiment, a method of producing genetically modified TFPI by a yeast expression system such as *Pichia.pastoris* expression system is provided in this invention. The method starts with an optimized mutant LTFPI sequence which is capable of expression in a yeast cell. In one embodiment, the optimized mutant LTFPI DNA sequence is a sequence represented by SEQ ID NO: 1. The optimized mutant LTFPI sequence can be provided by synthesis processes, for example by overlap-extension PCR process, chemical synthesis or some other PCR-based synthesis, which synthesize nucleotide constructs. Next, the optimized mutant LTFPI DNA sequence recombines with a plasmid, then the plasmid is transformed into the yeast cell. The transformed yeast cell is cultured and LTFPI expression is induced by adding methanol into the cultural media, and the expressed LTFPI is secreted into the cultural media. The optimized mutant LTFPI from supernatant of the cultured yeast cell is collected, separated and subsequently purified. The plasmid in this method can be any plasmid such as pPICZα, pPIC3.5K and PAO815, for the yeast expression system, typically, the plasmid is pPIC9k. The yeast in the yeast expression system can be any kind of yeast such as KM71, SMD1163 and X33, typically, the yeast is *Pichia.pastoris*, and the *Pichia.pastoris* is GS 115.

The step of using overlap-extension PCR to provide the optimized mutant TFPI sequence to the method of producing genetically modified TFPI is further described as the following: Several pairs of primers are prepared. Typically, 10 pairs of primers are prepared and provided according to table 1; both ends of the primers are attached with restriction endonuclease EcoRI and NotI; several steps of overlap-extension PCR are performed starting from middle position extending outward, typically, 10 steps of overlap-extension PCR are performed starting from middle position extending outward, in which the first step is performed with 10a and 10b as the primer and the template, and the subsequent steps of the overlap-extension PCR are performed using the product of the previous step as the template and corresponding primers according to table 1.

TABLE 1

| PCR Step | Primers | | Sequences | |
|---|---|---|---|---|
| 1 | 10a | 10b | SEQ ID NO: 3 | SEQ ID NO: 4 |
| 2 | 9a | 9b | SEQ ID NO: 5 | SEQ ID NO: 6 |
| 3 | 8a | 8b | SEQ ID NO: 7 | SEQ ID NO: 8 |
| 4 | 7a | 7b | SEQ ID NO: 9 | SEQ ID NO: 10 |
| 5 | 6a | 6b | SEQ ID NO: 11 | SEQ ID NO: 12 |
| 6 | 5a | 5b | SEQ ID NO: 13 | SEQ ID NO: 14 |
| 7 | 4a | 4b | SEQ ID NO: 15 | SEQ ID NO: 16 |
| 8 | 3a | 3b | SEQ ID NO: 17 | SEQ ID NO: 18 |

TABLE 1-continued

| PCR Step | Primers | | Sequences | |
|---|---|---|---|---|
| 9 | 2a | 2b | SEQ ID NO: 19 | SEQ ID NO: 20 |
| 10 | 1a | 1b | SEQ ID NO: 21 | SEQ ID NO: 22 |

Figure 1B:
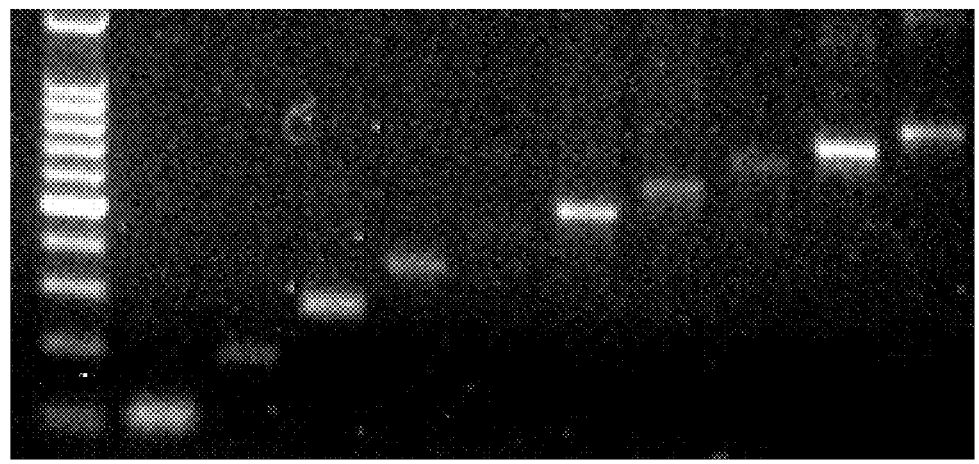
FIG. 1b shows electrophoresis of sequence segments synthesized by each step of overlap-extension PCR.

FIG. 1a depicts a diagram of typical 10 steps of synthesizing LTFPI by overlap-extension PCR (O-E PCR) from 10 pairs of primers (primer 10a, 10b through 1a, 1b). The result of the 10 steps O-E PCR is examined by electrophoresis. FIG. 1b depicts electrophoresis result of sequence segments synthesized by each step of overlap-extension PCR: DNA standard is in Lane 1, sequence segment synthesized with primers 10a and 10b by step 1 of O-E PCR is in Lane 2, sequence segment synthesized with primers 9a and 9b by step 2 of O-E PCR is in Lane 3, sequence segment synthesized with primers 8a and 8b by step 3 of O-E PCR is in Lane 4, sequence segment synthesized with primers 7a and 7b by step 4 of O-E PCR is in Lane 5, sequence segment synthesized with primers 6a and 6b by step 5 of O-E PCR is in Lane 6, sequence segment synthesized with primers 5a and 5b by step 6 of O-E PCR is in Lane 7, sequence segment synthesized with primers 4a and 4b by step 7 of O-E PCR is in Lane 8, sequence segment synthesized with primers 3a and 3b by step 8 of O-E PCR is in Lane 9, sequence segment synthesized with primers 2a and 2b by step 9 of O-E PCR is in Lane 10, and sequence segment synthesized with primers 1a and 1b by step 10 of O-E PCR is in Lane 11, which is the completely synthesized result sequence: SEQ ID NO. 1.

Figure 2:
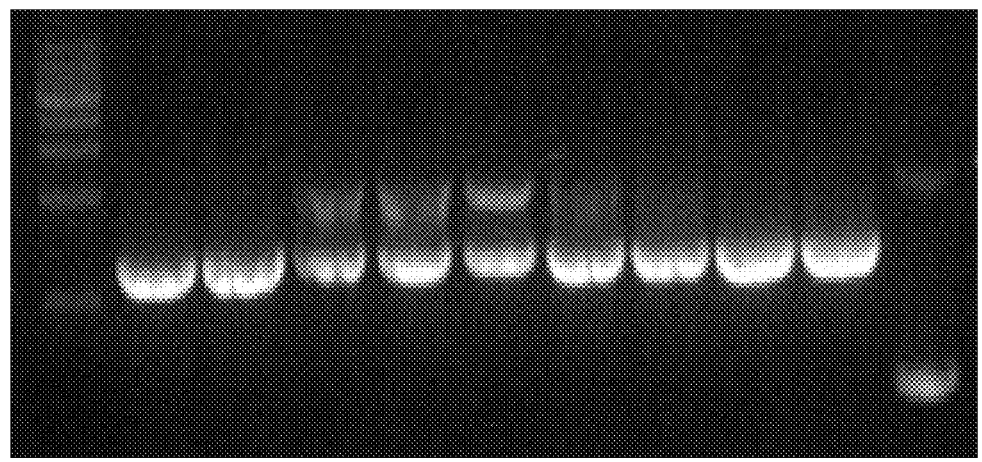
FIG. 2 shows electrophoresis result of detecting positive transformant in *Pichia.pastoris*.

The prepared copies of LTFPI sequences are screened and selected by *Pichia.pastoris* expression system. FIG. 2 depicts electrophoresis result of detecting positive transformant in *Pichia.pastoris*. DNA standard is in Lane 1, Mut$^S$ transformant is in Lane 2, Lane 3, Lane 8, Lane 9 and Lane 10, Mut$^+$ transformant is in Lane 4, Lane 5, Lane 6, Lane 7. GS115 from pPIC9K is in Lane 11, serving as blank control.

Figure 3:
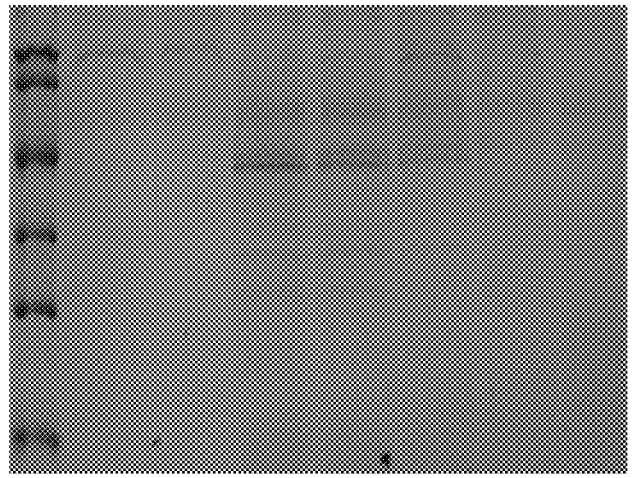
FIG. 3 shows SDS-PAGE result of induced expression of LTFPI.

After methanol induction, mutant LTFPI is expressed and secreted in to supernatant of cultural media. FIG. 3 is SDS-PAGE result showing induced expression of LTFPI: Protein standard is in Lane 1, LTFPI protein before induced expression is in Lane 2 and Lane 3, LTFPI protein after induced expression is shown in Lane 4 through Lane 8.

Figure 4:
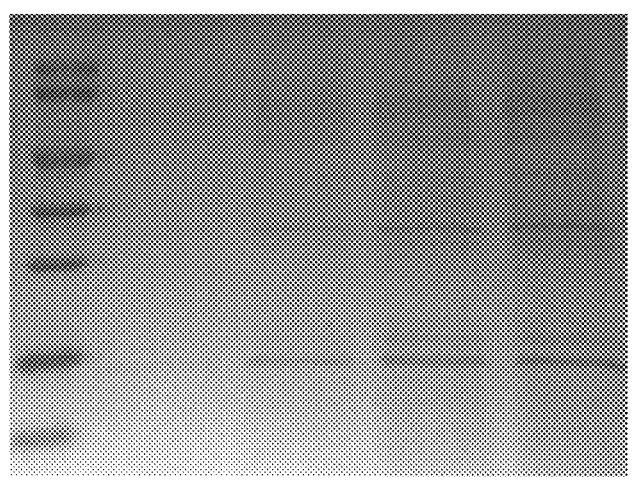
FIG. 4 shows SDS-PAGE result of LTFPI expression vs. inducing time of the expression.

The amount of LTFPI expressed is proportional to methanol induction time. FIG. 4 shows SDS-PAGE result of LTFPI expression vs. inducing time: Protein standard is in Lane 1, LTFPI protein expression after 12 hour induction is in Lane 2, LTFPI protein expression after 24 hour induction is in Lane 3, LTFPI protein expression after 36 hour induction is in Lane 4 and LTFPI protein expression after 48 hour induction is in Lane 5.

Figure 5:
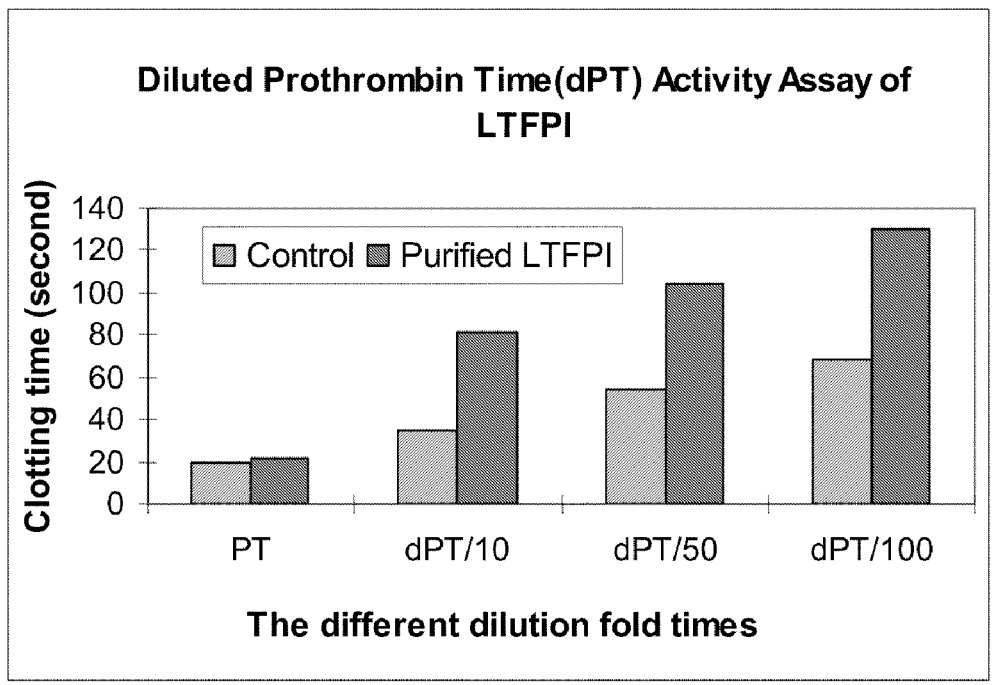
FIG. 5 shows the activity of LTFPI in term of prothrombin time determined by dPT assay.

The anticoagulation activity of LTFPI polypeptide produced by *Pichia.pastoris* expression system is tested by Diluted prothrombin time (dPT) assay or chemiluminescence assay. FIG. 5 shows the activity of LTFPI in term of prothrombin time determined by dPT assay. Series 1 is control, and series 2 is the sample containing LTFPI. Prothrombin time of control (without LTFPI) is shown in PT, dPT/10, dPT/50 and dPT/100 are prothrombin times with diluting thromboplastin standard solution in a vial with balanced saline to 10 times, 50 times and 100 times respectively. Briefly, standard reaction agents are prepared by diluting thromboplastin standard solution in vials with balanced saline to 10 times, 50 times and 100 times respectively, then adding 100 μL normal person's blood plasma sample to each of the vials, 100 μL thromboplastin standard solution and 10 μL LTFPI solution (750 μg/ml) into the vials, and coagulation times are recorded. The experiments are repeated 3 times and each group of the recorded time is averaged, and the data are plotted.

Figure 6:
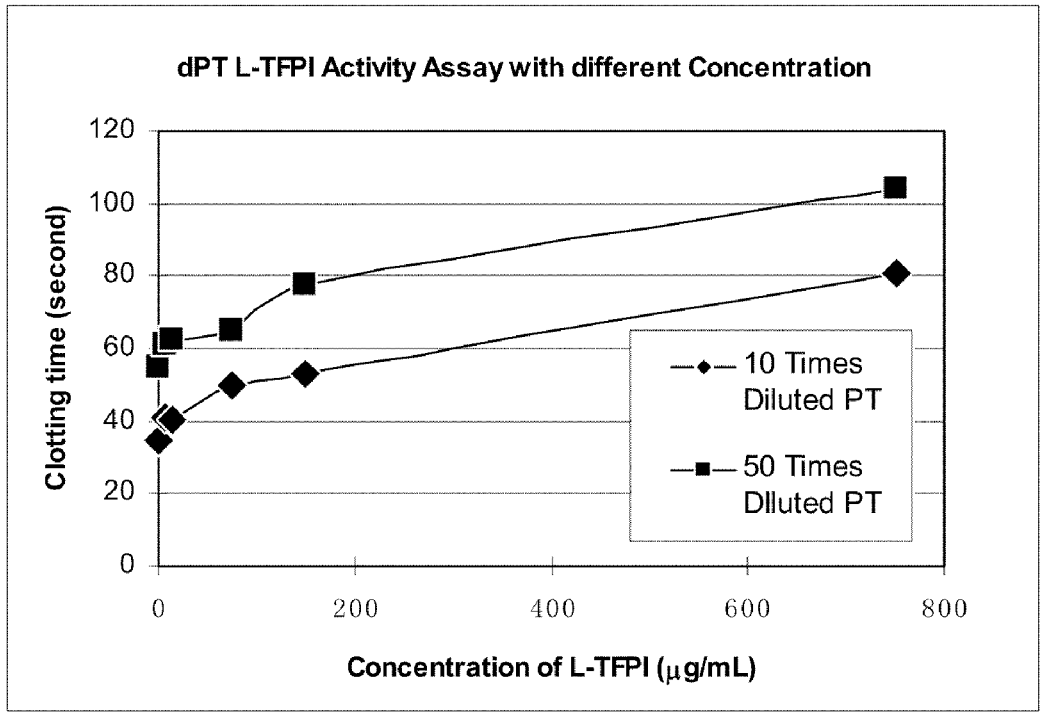
FIG. 6 shows the relationship of diluted prothrombin time vs. concentration of purified LTFPI polypeptide under 10 times diluted PT reagent and 50 times diluted PT reagent.

FIG. 6 shows the relationship of diluted prothrombin time vs. concentration of purified LTFPI protein under 10 times diluted PT reagent and 50 times diluted PT reagent. (Series 1 is purified LTFPI protein under 10 times diluted PT reagent and series 2 is purified LTFPI protein under 50 times diluted PT reagent). The top curve is diluted prothrombin times of various concentrations of LTFPI under condition of 50 times diluted PT reagent, below curve depicts diluted prothrombin times of various concentrations of LTFPI under condition of 10 times diluted PT reagent.

Thus a nucleotide sequence represented by SEQ ID NO: 1 which can be used to express a genetically modified LTFPI protein (SEQ ID NO: 2) for anticoagulation, is prepared. The LTFPI is characterized by the codons of the lysine at the carboxy-terminal sites 241, 254, 260 and 261 which are replaced by the codons of alanin and the codons of amino acid asparagine at glycosylation sites 117, 167, 228 and the codons of amino acid serine and threonine at glycosylation sites 174 and 175 which are substitutionally mutated.

Further, a pharmaceutical composition for anticoagulation can be prepared which comprises a pharmaceutically effective amount of genetically modified LTFPI protein encoded by a genetically modified LTFPI sequence represented by SEQ ID NO: 1, with a pharmaceutically acceptable carrier. The lysine at the carboxy-terminal sites 241, 254, 260 and 261 of genetically modified LTFPI protein are replaced by alanin and the amino acid asparagine at glycosylation sites 117, 167, 228 and the amino acid at serine and threonine glycosylation sites 174 and 175 are substitutionally mutated.

As used herein, the term "pharmaceutically acceptable carrier" refers to a medium which does not interfere with the effectiveness of the biological activity of the active ingredient and which is not toxic to the hosts to which it is administered.

As used herein, the term "pharmacologically effective amount" refers to the amount of protein or polypeptide administered to the host that results in reduction of morbidity and mortality resulting from the condition being treated. Conditions that may be treated include thrombogenesis caused by plaque ruptures in atherosclerosis, myocardial infarction, ischemia, cerebrovascular disease, pulmonary thromboembolism, deep vein thrombosis, DIC and sepsis. The exact amount administered depends on condition, severity, subject etc., but may be determined by routine methods. The term "pharmacologically effective amount" also refers to the amount of protein or polypeptide administered to the host that prevents morbidity and mortality resulting associated with a condition. Conditions that may be prevented include thrombogenesis caused by plaque ruptures in atherosclerosis, myocardial infarction, ischemia, cerebrovascular disease, pulmonary thromboembolism, deep vein thrombosis, DIC and sepsis. The exact amount administered depends on condition, severity, subject etc., but may be determined by routine methods.

EXAMPLES

Example 1

Site Mutation of TFPI and Optimization Of TFPI DNA Entire Sequence

The wild type TFPI sequence is mutated to obtain the mutated TFPI, represented by SEQ ID NO: 2, which has a long half life, has no glycosylation sites and is non immunogenic. The original amino acid residues asparagine at glycosylation sites 117, 167 and 228 are replaced by amino aid residues glutamine. The original amino acid residue serine at site 174 and amino acid residue threonine at site 175 are replaced by amino aid residues alanin. The original amino acid residues lysine at terminal sites 241, 254, 260 and 261 are replaced by amino aid residues alanin.

Next, a number of genetic codons which are favored by *Pichia.pastoris* are generated from the mutant TFPI sequence SEQ ID NO: 2 by using biological information sciences software Synthetic gene designer.

The number of genetic codons are further undergone a series of screening processes including yeast expression and testing anticoagulation activity, from which an optimized LTFPI DNA sequence represented by SEQ ID NO: 1 is obtained.

SEQ ID NO: 2 can be expressed in *Pichia.pastoris* (see FIG. 3 and FIG. 4 and description in Example 2) and has substantial anticoagulation activity as shown in FIG. 5 and FIG. 6.

Example 2

LTFPI Preparation and its Property Determination (1) Obtaining LTFPI Gene

Wild type TFPI gene is used as the template, and 10 pairs of primer to optimize the genetic codons favored by *Pichia.pastoris* are designed (See Table 1 for primer designs).

Both ends of the primers are attached with restrictive endonuclease EcoRI sequence and NotI sequence.

Overlap-extension PCR is used to extend the primers from both sides by 10 steps of PCR reactions. In 1st step of PCR, primers 10a and 10b act as mutual template and mutual primer. In the rest steps of PCR, the product from previous PCR step is the template for the next step of PCR. For example 9a and 9b, 8a and 8b . . . and so on are used as template to extend the TFPI sequence until the end of the 10 steps of the overlap-extension PCR reactions and the entire TFPI sequence is obtained.

FIG. 1. shows the process of the steps of overlap-extension PCR. The product of PCR is recovered and is connected to T carrier (pMD 19-T vector, from TaKaRa Co.) and the sequence is determined by sequencing. The final sequence product is the LTFPI gene optimized with genetic codons favored by *Pichia.pastoris*.

(2) Constructing Plasmid pPIC9K-LTFPI for Yeast Expression

Invitrongen Corporation's pPIC9K is used as yeast expression carrier. Yeast containing LTFPI gene (clones that are sequenced correctly) with T carrier is cultured in shake flasks. The plasmid is extracted and cleaved by double restriction endonuclease EcoRI and NotI. The expression vector is also cleaved by double restriction endonuclease EcoRI and NotI. After cleavage, the sequences are recovered by 1% agarose gel electrophoresis respectively. Connecting LTFPI gene sequence with pPIC9K, and the recombinant pPIC9K-LTFPI plasmid is obtained.

(3) Electrical Transformation of *Pichia.pastoris* GS115

Recombinant plasmid pPIC9K-TFPI is cleaved with SalI restriction endonuclease to get completely linearized recombinant plasmid.

The linearized recombinant plasmid is extracted with phenol/chloroform, and is purified with ethyl alcohol precipitation. The purified and precipitated linearized recombinant plasmid is then dissolved in sterilized double distilled water.

Ten μL of the above linearized recombinant plasmid (10~20 μg) sample is added by 80 μL competent *Pichia.pastoris* GS 115 and is mixed well, then the mixture is changed over to ice-cold 0.2 cm electrical transforming cup, and put on ice-bathing for 5 min.

Electric shock transformation parameters are set to: Voltage 1500V, capacitance 25 μF, resistance 200Ω);

The mixture is electric shocked one time, and 1 mL ice-cold 1 mol/L Sorbitol is added immediately, mixing well, then 600 μL of the transformate fluid is taken and spread onto MD plate (1.34% YNB, 4×10-5% Biotin, 2% Dextrose, 1.5% Agar). The plate is cultured at 30 degree C. for 48h until the growth of the monoclonal colony.

(4) Screening the Multi-Copy Positively Transformated Yeast Monoclonal Colony

Monoclonal yeast colonies from MD plate are selected and transferred to 96 holes cell cultural board, each of the holes of the cultural board contains 200 μL YPD cultural media, and the yeast is cultured at 30 degree C. for 24 h.

Ten μL cultured yeast is transferred to a new 96 holes cell culture board, each of the holes containing 190 μL YPD culture media, and is cultured at 30 degree C. for 24 h.

The previous steps are repeated 1 more time.

Multiple copies of 2 μL cultured yeast are transferred to YPD plates containing 0, 0.5, 1.0, 2.0, 4.0 g/L G418 respectively. Then the yeast is cultured at 30 degree C. until the monoclonal colony grows.

(5) Determining the Phenotype of Transformed Monoclonal Yeast

Monoclonal yeast from highly concentrated G418-YPD plate (approximately 107 cells) are selected. The yeast is inoculated to 20 μL 0.25% SDS solution, mixing well, then the solution is heated to 90 degree C. for 3min. The solution is centrifuged, 1 μL of the supernatant is taken as template for PCR reaction with upstream and downstream primers.

Total PCR reaction system is 50 L, including 1% Triton X-100.

PCR Reaction Condition:

The sample is at 95 degree C. denature for 2 min; at 95 degree C. denature for 60 second, at 55 degree C. annealing for 60 second, at 72 degree C. extending for 120 second, repeat the reactions for 30 cycles. Final step of PCR: the sample is at 72 degree C. extending for 5 min. Then the PCR product is taken out and kept at 4 degree C.

Based on the PCR result, the phenotype of transformed monoclonal yeast is determined:

Sample displays one band only (492 bp plus exogenous gene fragment 852 bp=1344 bp), the phenotype of transformed monoclonal yeast (Mut$^S$) is slow methanol user.

Sample displays two bands (the above described one band plus a 2.2 kb band), the phenotype of transformed monoclonal yeast (Mut$^+$) is fast methanol user. FIG. 2. shows the experiment result.

(6) Inducing the Expression of Recombinant LTFPI in *Pichia.pastoris*

*Pichia.pastoris* containing multi-copy of positive monoclonal LTFPI from highly concentrated G418-YPD plate is selected and inoculated onto 5 mL BMGY cultural media, shaking culture 30 degree C.×250r/min×12 h, grows to $OD_{600}$=5~6.

The cultural media is collected and centrifuged. The pellet from centrifugation is washed with sterilized distilled water two times, then is inoculated into BMMY cultural media to induce the expression of recombinant LTFPI in *Pichia.pastoris*.

Additional methanol 0.3% is supplied to the cultured *Pichia.pastoris* once every 8 hour. Cultured *Pichia.pastoris* is induced by methanol for 48 hours.

FIG. 3 shows the induced expression.

FIG. 4 shows the relationship between desired protein expression and the inducing time.

(7) LTFPI Fermentation Expression

Mut$^+$ type multi-copy LTFPI positive monoclonal *Pichia.pastoris* colony is selected and inoculated into 5 mL YPD cultural media The cultural media is shake cultured at 30 degree C.×250 r/min for 12 h, and first-level seed culture is obtained.

The first-level seed culture is inoculated into 200 mL BMGY cultural media (1% Yeast Extract, 2% Peptone, 100mmol/L Potassium Phosphate, 1.34% YNB, 4×10-5% Biotin, 1% Glycerol), The cultural media is shake cultured at 30d egree C.×250 r/min for 16 h, to $OD_{600}$=5~6, and second-level seed culture is obtained.

The second-level seed culture is inoculated into 4 L low salt fermentation cultural media, of which each liter contains 0.93 g $CaSO_4.2H_2O$, 18.2 g $K_2SO_4$, 7.27g $MgSO_4$, 26.7 mL 85% $H_3PO_4$, 4.13 g KOH, 40 g Glycerol, 1.47 g Sodium citrate tribasic dihydrate, 2 mL PTM1 solution, pH adjusted to 5.0 with 28% ammonia.

Fermentation Cultural Condition is as Following:

Temperature 30 degree C., stirring speed 600 r/min, oxygen dissolved 35%, automatically adding ammonia to maintain pH5.0.

The media is cultured continuously for 18 h to $OD_{600}$=70~80, till oxygen dissolved in the media rises quickly, and glycerol is exhausted from the media, then 50% glycerol is added to the media at the speed 80 mL/h, for time 2~3 h, until the cultural media is $OD_{600}$=150~160, addition of glycerol to the media is stopped. Wait until all the glycerol in the media is exhausted completely, then start to add methanol immediately during the first 2-3 hours, Set the feed rate to 3.6 ml/hr per liter initial fermentation volume, When the culture is fully adapted to methanol utilization, and is limited on methanol feeding, maintain the lower methanol feed rate under limited conditions for at least 1 hour after adaptation before doubling the feed. The feed rate is then doubled to ~7.3 ml/hr/liter initial fermentation volume. After 2 hours at the 7.3 ml/hr/liter feed rate, increase the methanol feed rate to ~10.9 ml/hr per liter initial fermentation volume. This feed rate is maintained throughout the remainder of the fermentation.

After methanol inducing expression for 40 hours, the fermentation is stopped, and the cultural media is collected from the fermentation pot, and the collected cultural media is centrifuged immediately.

The supernatant is collected and purified after centrifugation, and the precipitated *Pichia.pastoris* is separated.

The fermentation parameter is as follows: Temperature 30 degree C., oxygen capacity is controlled to 35±5%, pH=5.0, stirring speed is correspondent to DO (Dissolved Oxygen).

Example 3

Purification Technique (1) Concentration Via Ultra Filter

Collected 18 L of supernatant from the fermentation cultural media is centrifuged, and is filtered through Millipore 50 KD ultra filter unit, then it is further concentrated through 8 KD ultra filter unit to 0.5 L, the supernatant is concentrated approximately 40 times and becomes superfiltri-concentrated fluid after the filtering concentration process.

(2) Desalinization Via Gel Filtration

Super-filtri-concentrated fluid is added to Sephadex X-100 column (after 20 mmol/L PB (pH7.0) balanced) and passes through the column, then the column is eluted with PB at the speed of flow 8ml/min, and active peaks are collected.

(3) Q-Sepharose Fast Flow Column Chromatography

Active peaks collected from gel filtration is collected and is added to Q-Sepharose F.F column (Pharmacia Corporation) balanced with 20 time of column volume equilibrium liquid (20 mmol/L PB pH7.0), which is pre-balanced with 50 mmol/L PB (pH 7.0) and passes the column. Anticoagulation active parts are collected after the column filtration.

(4) Heparin Sepharose CL-6B Chromatography

Desired peaks are collected and are purified on heparin affinity chromatographic column, the eluted peak components are analyzed, and the sample protein is quantified with BCA-Protein Quantitative Analysis Kit method.

The sample undergoes 12% SDS-PAGE electrophoresis, then it is stained by Coomassie brilliant blue.

The sample purity is analyzed by scanning.

The sample is packaged, freeze-dried, and stored under –80 degree C.

Chromatograph operations in method of this invention disclosure are all conventional operation.

Example 4

LTFPI Activity Testing (1) Diluted Prothrombin time (dPT) to Determine LTFPI Activity Anticoagulation activity of LTFPI is determined by Dilute prothrombin time.

Thromboplastin standard solution is diluted with balanced saline (physiological saline) to 10, 100, 200 and 500 times, then is stored under 37 degree C. Blood plasma samples from a normal person, each of them is 100 μL, are added to 100 μL thromboplastin standard solution with various concentrations, then 10 μL protein solution with various concentrations is added into each of the blood plasma samples.

The samples are cultured in 37 degree C. for 1 min, and 10 μL $CaCl_2$ solution (250 mmol/L) is added into each of the samples, The blood plasma coagulation time is recorded.

Taking 3 experiments data an averaging them to get mean values, and recording the experimental result, All reagents in the experiment are preheated at 37 degree C., and the entire experiment is completed in 2 hours.

FIG. 5 shows purified LTFPI polypeptide activity against control using diluted prothrombin time assay.

FIG. 6 shows the relationship of prothrombin time vs concentration of purified LTFPI polypeptide under 10 times diluted PT reagent and 50 times diluted PT reagent.

(2) Determining LTFPI Activity by Chemiluminescence Assay

The first Kunitz domain of TFPI is able to bind to FVIIa/TF complex, the second Kunitz domain of TFPI is able to bind to FXa and forms inactive FVIIa/TF/TFPI/FXa complex. After LTFPI is cultured with TF/FVIIa and FX, the activity of remaining TF/FVIIa can be determined by color substrate Spectrozyme FXa, thus the activity of LTFPI can be deducted indirectly. After purification the activity of LTFPI detected is 0.6 unit/ml, which is equal to 3 times of the activity of the standard.

What is claimed is:

1. A method of producing Long-half-life Tissue Factor Pathway Inhibitor (LTFPI) DNA represented by SEQ ID NO: 1 comprising:
   (a) providing a synthesized polynucleotide represented by SEQ ID NO: 1 which is optimized for expression in a *Pichia pastoris* cell;
   (b) recombining said polynucleotide with a plasmid;
   (c) transforming the plasmid into the *Pichia pastoris* cell;
   (d) culturing the transformed *Pichia pastoris* cell;
   (e) collecting from supernatant of said cell the polypeptide encoded by the polynucleotide represented by SEQ ID NO: 1; and
   (f) separating and purifying the collected polypeptide.

2. The method of producing the DNA of claim 1, wherein the plasmid is pPIC9k.

3. The method of producing the DNA of claim 1, wherein *Pichia pastoris* is GS115.

4. The method of producing the DNA of claim 1, wherein the step of providing the synthesized polynucleotide represented by SEQ ID NO: 1 comprises at least one step of overlap-extension PCR.

5. The method of producing the DNA of claim 1, wherein the step of providing the polynucleotide represented by SEQ ID NO: 1 comprises:
   (a) providing 10 pairs of primers according to Table 1;
   (b) attaching restriction endonuclease EcoRI and NotI onto both ends of each of said primers;
   (c) performing 10 steps of overlap-extension PCR starting from the middle position extending outward: (i) performing the first step with the template and primers 10a and 10b of Table 1; (ii) performing the immediately subsequent step of the overlap-PCR using the product of the immediately preceding step as the template and corresponding primers according to Table 1.

6. A synthesized polynucleotide optimized for eukaryotic expression system, wherein said encoded polypeptide is capable of anticoagulation comprising:

a synthesized LTFPI polynucleotide represented by SEQ ID NO: 1 which is mutated from human wild type Tissue Factor Pathway Inhibitor (TFPI) at N-glycosylation sites 117, 167, and 228, glycosylation sites 174 and 175, and the carboxy-terminal sites 241, 254, 260 and 261; wherein the codons at sites 117, 167, and 228 encode amino acid glutamine, the codons at sites 174 and 175 encode amino acid alanine, and the codons at sites 241, 254, 260 and 261 encode amino acid alanine.

* * * * *

SEQUENCE LISTING

<160> NUMBER OF SEQ ID NOS: 22

<210> SEQ ID NO 1
<211> LENGTH: 831
<212> TYPE: DNA
<213> ORGANISM: Artificial Sequence
<220> FEATURE:
<223> OTHER INFORMATION: mutant LTFPI sequence derived from wild type
      TFPI
<220> FEATURE:
<221> NAME/KEY: exon
<222> LOCATION: (1)..(831)

<400> SEQUENCE: 1

```
gac tct gaa gaa gat gag gaa cac aca atc atc acc gat acc gaa ttg      48
Asp Ser Glu Glu Asp Glu Glu His Thr Ile Ile Thr Asp Thr Glu Leu
1               5                   10                  15 cct ccc ctt aag ttg atg cat tct ttc tgt gct ttc aaa gct gac gac      96
Pro Pro Leu Lys Leu Met His Ser Phe Cys Ala Phe Lys Ala Asp Asp
            20                  25                  30 ggt cca tgt aag gcc att atg aag aga ttc ttc ttt aat atc ttt act     144
Gly Pro Cys Lys Ala Ile Met Lys Arg Phe Phe Phe Asn Ile Phe Thr
        35                  40                  45 aga cag tgt gaa gaa ttt att tac gga ggt tgt gaa ggt aac cag aat     192
Arg Gln Cys Glu Glu Phe Ile Tyr Gly Gly Cys Glu Gly Asn Gln Asn
    50                  55                  60 agg ttc gaa tcg ttg gaa gaa tgt aag aaa atg tgt acc cgt gat aac     240
Arg Phe Glu Ser Leu Glu Glu Cys Lys Lys Met Cys Thr Arg Asp Asn
65                  70                  75                  80 gcc aac aga att att aaa aca act ttg cag cag gaa aag cca gac ttt     288
Ala Asn Arg Ile Ile Lys Thr Thr Leu Gln Gln Glu Lys Pro Asp Phe
                85                  90                  95 tgc ttc ttg gaa gag gat cca gga att tgt cgt ggt tac atc aca aga     336
Cys Phe Leu Glu Glu Asp Pro Gly Ile Cys Arg Gly Tyr Ile Thr Arg
            100                 105                 110 tac ttc tat aat cag cag act aaa caa tgc gaa aga ttc aag tat gga     384
Tyr Phe Tyr Asn Gln Gln Thr Lys Gln Cys Glu Arg Phe Lys Tyr Gly
        115                 120                 125 gga tgc ttg gga aat atg aac aat ttt gaa acg ttg gag gaa tgc aag     432
Gly Cys Leu Gly Asn Met Asn Asn Phe Glu Thr Leu Glu Glu Cys Lys
    130                 135                 140 aat ata tgt gaa gat gga cca aat gga ttc cag gtt gac aat tat ggt     480
Asn Ile Cys Glu Asp Gly Pro Asn Gly Phe Gln Val Asp Asn Tyr Gly
145                 150                 155                 160 acc caa tta aat gct gta cag aac tca ttg act ccc cag gct gca aag     528
Thr Gln Leu Asn Ala Val Gln Asn Ser Leu Thr Pro Gln Ala Ala Lys
                165                 170                 175 gtc cca tcc ttg ttt gag ttc cat gga cca tcc tgg tgt ttg acc cct     576
Val Pro Ser Leu Phe Glu Phe His Gly Pro Ser Trp Cys Leu Thr Pro
            180                 185                 190 gcc gat cgt gga ttg tgt aga gct aat gaa aac aga ttc tat tac aat     624
Ala Asp Arg Gly Leu Cys Arg Ala Asn Glu Asn Arg Phe Tyr Tyr Asn
        195                 200                 205 tct gtt atc ggg aaa tgt aga ccg ttt aag tat tct gga tgt gga gga     672
Ser Val Ile Gly Lys Cys Arg Pro Phe Lys Tyr Ser Gly Cys Gly Gly
    210                 215                 220 aac gag aac cag ttc acc tct aag cag gag tgt tta agg gct tgt aaa     720
Asn Glu Asn Gln Phe Thr Ser Lys Gln Glu Cys Leu Arg Ala Cys Lys
225                 230                 235                 240 gct gga ttt att cag cgt atc agt aaa ggt ggt ctt att gct aca aaa     768
Ala Gly Phe Ile Gln Arg Ile Ser Lys Gly Gly Leu Ile Ala Thr Lys
```

```
                245                 250                 255
cgt aaa aga gca gcc caa aga gtc aag att gcc tat gaa gag atc ttt   816
Arg Lys Arg Ala Ala Gln Arg Val Lys Ile Ala Tyr Glu Glu Ile Phe
            260                 265                 270 gtt aag aac atg taa                                                831
Val Lys Asn Met
        275

<210> SEQ ID NO 2
<211> LENGTH: 276
<212> TYPE: PRT
<213> ORGANISM: Artificial Sequence
<220> FEATURE:
<223> OTHER INFORMATION: mutant LTFPI sequence derived from wild type
      TFPI
<220> FEATURE:
<221> NAME/KEY: MISC_FEATURE
<222> LOCATION: (1)..(276)

<400> SEQUENCE: 2

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Gln Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Ile Cys Glu Asp Gly Pro Asn Gly Phe Gln Val Asp Asn Tyr Gly
145                 150                 155                 160

Thr Gln Leu Asn Ala Val Gln Asn Ser Leu Thr Pro Gln Ala Ala Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
    210                 215                 220

Asn Glu Asn Gln Phe Thr Ser Lys Gln Glu Cys Leu Arg Ala Cys Lys
225                 230                 235                 240

Ala Gly Phe Ile Gln Arg Ile Ser Lys Gly Gly Leu Ile Ala Thr Lys
                245                 250                 255

Arg Lys Arg Ala Ala Gln Arg Val Lys Ile Ala Tyr Glu Glu Ile Phe
            260                 265                 270

Val Lys Asn Met
        275

<210> SEQ ID NO 3
```

```
<211> LENGTH: 57
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(57)

<400> SEQUENCE: 3
tgcgaaagat tcaagtatgg aggatgcttg ggaaatatga acaatttga aacgttg        57

<210> SEQ ID NO 4
<211> LENGTH: 58
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(58)

<400> SEQUENCE: 4
aacctggaat ccatttggtc catcttcaca tatattcttg cattcctcca acgtttca      58

<210> SEQ ID NO 5
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 5
ggttacatca caagatactt ctataatcag cagactaaac aatgcgaaag attcaa        56

<210> SEQ ID NO 6
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 6
caatgagttc tgtacagcat ttaattgggt accataattg tcaacctgga atccat        56

<210> SEQ ID NO 7
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 7
ccagactttt gcttcttgga agaggatcca ggaatttgtc gtggttacat cacaag        56

<210> SEQ ID NO 8
<211> LENGTH: 56
<212> TYPE: DNA
<213> ORGANISM: Artificial Sequence
<220> FEATURE:
<223> OTHER INFORMATION: Synthesized Construct
```

```
<220> FEATURE:
<221> NAME/KEY: misc_feature
<222> LOCATION: (1)..(56)

<400> SEQUENCE: 8
atggaactca aacaaggatg ggacctttgc agcctgggga gtcaatgagt tctgta          56

<210> SEQ ID NO 9
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 9
aacgccaaca gaattattaa acaactttg cagcaggaaa agccagactt ttgctt           56

<210> SEQ ID NO 10
<211> LENGTH: 57
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(57)

<400> SEQUENCE: 10
tacacaatcc acgatcggca ggggtcaaac accaggatgg tccatggaac tcaaaca         57

<210> SEQ ID NO 11
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 11
ttcgaatcgt tggaagaatg taagaaaatg tgtacccgtg ataacgccaa cagaat          56

<210> SEQ ID NO 12
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 12
cccgataaca gaattgtaat agaatctgtt ttcattagct ctacacaatc cacgat          56

<210> SEQ ID NO 13
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 13
```

```
aagaatttat ttacggaggt tgtgaaggta accagaatag gttcgaatcg ttggaa         56
```

<210> SEQ ID NO 14
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 14

```
tcgtttcctc cacatccaga atacttaaac ggtctacatt tcccgataac agaatt         56
```

<210> SEQ ID NO 15
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 15

```
tatgaagaga ttcttcttta atatctttac tagacagtgt gaagaattta tttacg         56
```

<210> SEQ ID NO 16
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 16

```
tacaagccct taaacactcc tgcttagagg tgaactggtt ctcgtttcct ccacat         56
```

<210> SEQ ID NO 17
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 17

```
ttctgtgctt tcaaagctga cgacggtcca tgtaaggcca ttatgaagag attctt         56
```

<210> SEQ ID NO 18
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 18

```
aataagacca cctttactga tacgctgaat aaatccagct ttacaagccc ttaaac         56
```

<210> SEQ ID NO 19

-continued

```
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 19
tcaccgatac cgaattgcct ccccttaagt tgatgcattc tttctgtgct ttcaaa        56

<210> SEQ ID NO 20
<211> LENGTH: 56
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(56)

<400> SEQUENCE: 20
gcaatcttga ctctttgggc tgctctttta cgttttgtag caataagacc accttt        56

<210> SEQ ID NO 21
<211> LENGTH: 58
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(58)

<400> SEQUENCE: 21
tacgtagaat tcgactctga agaagatgag gaacacacaa tcatcaccga taccgaat      58

<210> SEQ ID NO 22
<211> LENGTH: 58
<212> TYPE: DNA
<213> ORGANISM: Artificial Sequence
<220> FEATURE:
<223> OTHER INFORMATION: Synthesized Construct
<220> FEATURE:
<221> NAME/KEY: misc_feature
<222> LOCATION: (1)..(58)

<400> SEQUENCE: 22
attcgcggcc gcttacatgt tcttaacaaa gatctcttca taggcaatct tgactctt      58
```